US007410464B2

(12) United States Patent
Ein-Gal

(10) Patent No.: US 7,410,464 B2
(45) Date of Patent: *Aug. 12, 2008

(54) WAVE GENERATING DEVICE

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 276 days.

This patent is subject to a terminal disclaimer.

(21) Appl. No.: 10/160,073

(22) Filed: Jun. 4, 2002

(65) Prior Publication Data

US 2003/0225346 A1 Dec. 4, 2003

(51) Int. Cl.
*A61B 8/00* (2006.01)

(52) U.S. Cl. ....................... 600/437; 600/439; 600/459; 600/472; 601/2; 601/3; 601/4; 73/642; 362/341

(58) Field of Classification Search ................. 600/407, 600/437, 439, 459, 472; 601/2, 4; 73/642; 362/341

See application file for complete search history.

(56) References Cited

U.S. PATENT DOCUMENTS

| | | | | | |
|---|---|---|---|---|---|
| 3,916,675 | A | * | 11/1975 | Perdijon | 73/642 |
| 3,974,684 | A | * | 8/1976 | Roule et al. | 73/642 |
| 4,151,752 | A | * | 5/1979 | Perdijon | 73/642 |
| 4,423,637 | A | * | 1/1984 | Soloway | 73/642 |
| 4,776,342 | A | * | 10/1988 | Zimmer | 600/437 |
| 5,117,832 | A | * | 6/1992 | Sanghvi et al. | 600/459 |
| 5,143,073 | A | * | 9/1992 | Dory | 600/439 |
| 5,193,527 | A | * | 3/1993 | Schafer | 601/2 |
| 5,406,074 | A | * | 4/1995 | Grisell | 250/221 |
| 5,669,708 | A | * | 9/1997 | Mashima et al. | 362/341 |
| 5,844,140 | A | * | 12/1998 | Seale | 73/633 |
| 6,190,318 | B1 | * | 2/2001 | Bab et al. | 600/437 |
| 6,267,734 | B1 | * | 7/2001 | Ishibashi et al. | 601/2 |
| 6,565,520 | B1 | * | 5/2003 | Young | 601/2 |
| 2002/0012897 | A1 | * | 1/2002 | Tingley et al. | 433/215 |
| 2003/0050559 | A1 | * | 3/2003 | Ein-Gal | 600/437 |
| 2006/0287698 | A1 | * | 12/2006 | Ein-Gal | 607/103 |

* cited by examiner

*Primary Examiner*—Brian L. Casler
*Assistant Examiner*—Baisakhi Roy
(74) *Attorney, Agent, or Firm*—Dekel Patent Ltd.; David Klein

(57) ABSTRACT

A wave generating device including a wave transducer adapted to generate an energy wave, and a beam shaping device defined by revolution of a curve about an axis of revolution, the curve being arranged with respect to the transducer in a plane of the curve so as to focus a wave emanating from the transducer towards the beam shaping device to a focal point lying in the plane, the curve having an axis of symmetry in the plane, wherein the axis of revolution is generally not collinear with the axis of symmetry.

18 Claims, 4 Drawing Sheets

WAVE GENERATING DEVICE

FIELD OF THE INVENTION

The present invention relates to generation and focusing of energy waves in general, e.g., acoustic waves, and particularly to a wave generating device, useful in medical treatments, such as but not limited to, extracorporeal shockwave treatment (ESWT), and other non-medical uses, such as but not limited to, non-destructive testing of structures.

BACKGROUND OF THE INVENTION

Generation and focusing of energy waves, such as acoustic waves (or shockwaves, the terms being used interchangeably throughout) for purposes of medical treatment such as stone fragmentation or orthopedic treatment are accomplished through a variety of methods. Each method incorporates acoustic wave generation and associated focusing apparatus.

The prior art may be classified according to the geometry of the acoustic wave generation and associated focusing:

a. Point source and ellipsoidal reflector: A point source typically comprises electrohydraulic apparatus. Fast discharges of electrical energy between tips of closely spaced electrodes give rise to a sequence of spherical waves in a propagation liquid. The electrodes are arranged with respect to an ellipsoidal reflector, which has two focal points. The electrical energy is discharged at the first focus, and the waves are focused onto the second focus.

b. Planar source and acoustic lens: A planar source typically comprises electromagnetic apparatus. A thin circular membrane applies pressure to the propagation liquid by being jolted or repelled away from a planar coil. Fast discharges of electrical energy into the coil and the associated rapid changes in the magnetic field induce currents in the membrane, turning it into a magnet with a polarization opposite to that of the coil. The ensuing repulsions of the membrane, which is in close contact with the propagation liquid, generate the acoustic waves. The waves are then focused by a lens to a target located at the focus of the lens.

c. Cylindrical source and parabolic reflector: The cylindrical source generates an acoustic wave that emanates radially outwards from the longitudinal periphery of the cylinder. For example, a coil may be mounted on a cylindrical support and a cylindrical membrane. The coil may be pushed or repelled radially, gives rise to outwardly propagating cylindrical waves. A parabolic reflector focuses the waves into a point on the cylindrical axis of the system.

d. Spherical source: Spherical waves may be generated by an array of piezo-electric transducers or by an electromagnetic approach with a spherical membrane being repulsed inwardly into the propagation liquid. No further focusing is required.

In general, the spatial geometry of a focused wave generation device may be described by a planar geometry (e.g., a section of the device and its associated focal point), and by an axis of revolution used to form the spatial geometry of the device. For example, a partial ellipse with two associated foci provides the required planar geometry: lines emanating from one focus are reflected by the ellipse and converge on the focal point, with equal traveling distance. The spatial geometry of the focused wave generation device is obtained by revolving the planar geometry about the axis of symmetry of the partial ellipse.

Planar geometries of known focused wave generators comprise an axis of symmetry that is collinear with the axis of revolution used to form the spatial geometry of the focused wave generation. Consequently, prior art devices may have circularly symmetric spatial geometries and associated circular waves apertures that are sub-optimal for many applications.

SUMMARY OF THE INVENTION

The present invention seeks to provide wave generating devices with novel geometry. The wave generating devices may focus energy waves, such as but not limited to, acoustic waves or microwaves, in a manner heretofore not possible with prior art reflectors, thereby providing new possibilities of treatment modalities in medical uses, such as but not limited to, extracorporeal shockwave treatment (ESWT). The invention also has non-medical applications, such as but not limited to, non-destructive testing of structures.

There is thus provided in accordance with a preferred embodiment of the invention a wave generating device including a wave transducer adapted to generate an energy wave, and a beam shaping device defined by revolution of a curve about an axis of revolution, the curve being arranged with respect to the transducer in a plane of the curve so as to focus a wave emanating from the transducer towards the beam shaping device to a focal point lying in the plane, the curve having an axis of symmetry in the plane, wherein the axis of revolution is generally not collinear with the axis of symmetry.

In accordance with a preferred embodiment of the invention the wave transducer is formed by a shape revolved about the same axis of revolution. The beam shaping device may comprise a reflector or a lens, for example.

Further in accordance with a preferred embodiment of the invention the curve includes a portion of a conic section, such as but not limited to, at least a portion of at least one of a parabola, an ellipse, a circle and a hyperbola.

In accordance with a preferred embodiment of the invention a plurality of the beam shaping devices are arranged symmetrically about a common reference axis.

Further in accordance with a preferred embodiment of the invention the common reference axis coincides with the axis of revolution.

Still further in accordance with a preferred embodiment of the invention the focal points of the beam shaping devices generally coincide or do not coincide.

Additionally in accordance with a preferred embodiment of the invention a locus of the focal points of the beam shaping devices generally lies or does not lie in a single plane.

In accordance with a preferred embodiment of the invention one of the beam shaping devices is movable independently of another of the beam shaping devices.

Further in accordance with a preferred embodiment of the invention one of the beam shaping devices is formed by revolution about an axis of revolution which is distanced differently from its wave transducer than the distance from the axis of revolution to the wave transducer of another of the beam shaping devices.

Still further in accordance with a preferred embodiment of the invention a cross-section of the wave transducer in the plane includes a straight or curved edge.

In accordance with a preferred embodiment of the invention a cross-section of the wave transducer in the plane includes two portions distanced from each other and symmetrical about the axis of symmetry.

There is also provided in accordance with a preferred embodiment of the invention a wave generating device including a wave transducer adapted to generate an energy wave, and a beam shaping device including a curve arranged with respect to the transducer in a plane of the curve so as to focus a wave emanating from the transducer towards the beam shaping device to a focal point lying in the plane, the curve having an axis of symmetry in the plane, wherein the wave transducer is formed by a shape revolved about an axis of revolution which is generally not collinear with the axis of symmetry. The beam shaping device may also be defined by revolution of the curve about the same axis of revolution.

There is also provided in accordance with a preferred embodiment of the invention a system including a wave transducer adapted to generate an energy wave, a beam shaping device defined by revolution of a curve about an axis of revolution, the curve being arranged with respect to the transducer in a plane of the curve so as to focus a wave emanating from the transducer towards the beam shaping device to a focal point lying in the plane, the curve having an axis of symmetry in the plane, wherein the axis of revolution is generally not collinear with the axis of symmetry, and an imaging probe adapted to provide images at least in a vicinity of the focal point. The wave transducer and imaging probe may also be defined by revolution of the curve about the same axis of revolution.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
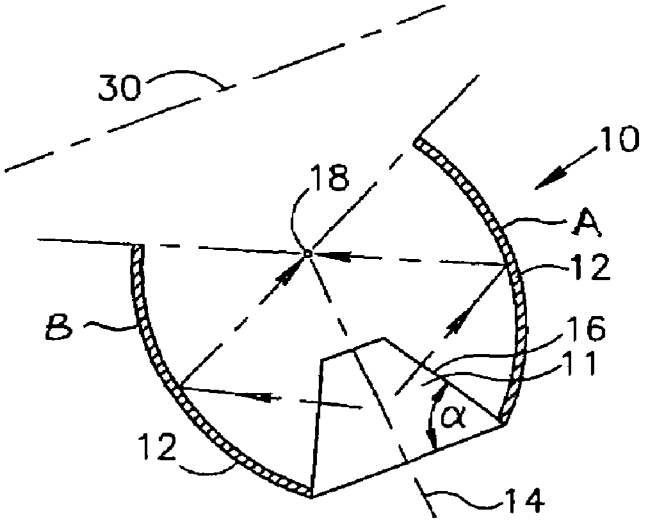
FIG. 1 is a simplified cross-sectional illustration of a wave generating device, comprising a wave transducer and two symmetric portions of parabolas.

Reference is now made to FIG. 1, which is a simplified cross-sectional illustration of a wave generating device 10, comprising a wave transducer 11 and two portions of parabolas 12 placed symmetrically about an axis of symmetry 14.

Wave transducer 11 may be a non-point acoustic wave transducer with a repulsive member 16 disposed on outer contour of a support. In general, the support is characterized by an angle $\alpha$ that defines the shape of the support. For example, if angle $\alpha=90°$, then the support is cylindrical. If angle $\alpha<90°$, then the support is conical. The present invention is not limited to any particular value of angle $\alpha$. Repulsive member 16 may generate an energy (e.g., acoustic) wave that emanates outwards from the support. For example, repulsive member 16 may comprise a coil or membrane mounted on the support. Repulsive member 16 may be pushed or repelled, giving rise to outwardly propagating waves. Parabolic portions 12 may focus the waves generated by wave transducer 11 to a focal point 18 situated on axis of symmetry 14, as is now explained.

As is well known from the definition of a parabolic surface, any ray emanating from the focal point 18 of the parabola that impinges upon the parabola is reflected from the parabola parallel to the axis of symmetry of the parabola. The converse is also true: any ray parallel to the axis of symmetry of the parabola, which impinges upon the parabola, is reflected to focal point 18. Accordingly, the contour of wave transducer 11 may thus be arranged such that rays that propagate perpendicularly away from the contour are parallel to the axis of symmetry of each parabolic portion 12, as seen in FIG. 1.

Figure 2:
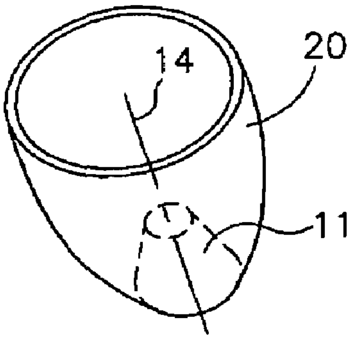
FIG.2 PRIOR ART
FIG. 2 is a simplified pictorial illustration of a parabolic reflector of the prior art formed by revolving the parabolic portions shown in FIG. 1 about their axis of symmetry, with the wave transducer lying along the axis of symmetry.

Reference is now made to FIG. 2. A parabolic reflector 20 of the prior art may be formed by revolving the parabolic portions 12 about their axis of symmetry 14, with wave transducer 11 lying along the axis of symmetry 14. The inner volume of reflector 20 may be filled with a propagation liquid (not shown), and the open end of reflector 20 may be covered with a membrane (not shown). The wave device so formed may be placed against or near a target (not shown), which it is desired to treat. Waves generated by wave transducer 11 may propagate through the propagation liquid and membrane towards the focal point 18, located in the target.

Figure 3:
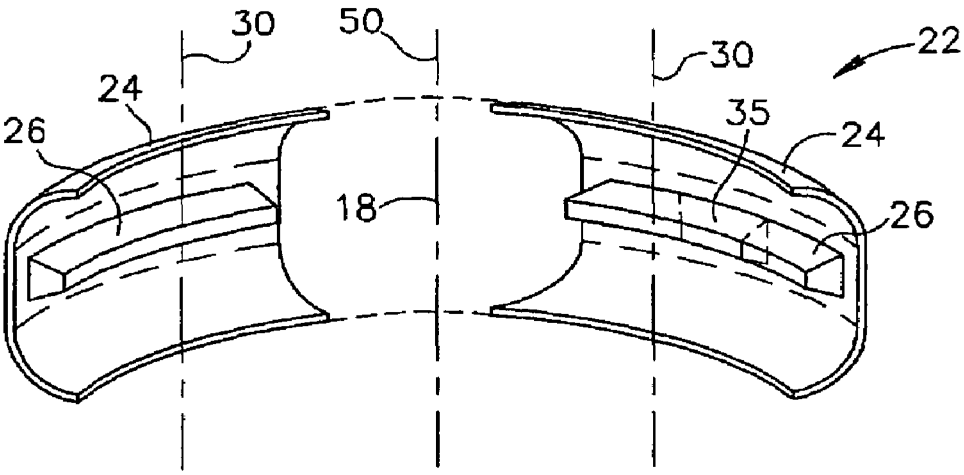
FIG. 3 is a simplified illustration of a wave generating device constructed and operative in accordance with one embodiment of the invention, comprising beam shaping devices (e.g., reflector segments) each formed by revolving the two symmetric parabolic portions of FIG. 1 about an axis of revolution different from their axis of symmetry.

Reference is now made to FIG. 3, which illustrates a wave generating device 22 constructed and operative in accordance with one embodiment of the invention. Wave generating device 22 may comprise a plurality of beam shaping devices 24, shaped as reflector segments. Each beam shaping device 24 may be formed by revolving the two symmetric parabolic portions 12 of FIG. 1 about an axis of revolution 30 (also shown in FIG. 1), which is different from (not collinear with) axis of symmetry 14. For example, in the illustrated embodiment, axis of revolution 30 is generally perpendicular with axis of symmetry 14.

A wave transducer 26 may be formed by the shape of wave transducer 11 of FIG. 1 revolved about the same axis of revolution 30. In the illustrated embodiment, the cross-section of wave transducer 26 in this plane comprises a straight edge, as seen in the shape of wave transducer 11 in FIG. 1. Moreover, in the illustrated embodiment, the cross-section of wave transducer 26 comprises two portions (denoted by letters A and B in FIG. 1) distanced from each other and symmetrical about axis of symmetry 14. An imaging probe 35 (shown in dashed lines in FIG. 3), such as but not limited to an X-ray probe, may be introduced through a hollow space of wave transducer 26. As will be shown and described in FIGS. 6 and 7, the cross-section of the wave transducer may comprise a curved edge (e.g., an "extruded" point source) or any other shape. Imaging probe 35 and wave generating device 10 may form a system for delivering wave energy to a site, such as a focal point, and imaging the site.

In general, beam shaping device 24 and/or wave transducer 26 and imaging probe 35 may be defined by revolution of a curve about axis of revolution 30. In the case of beam shaping device 24, the curve may comprise, without limitation, a portion of a conic section, such as in this example, a parabola.

As seen in FIG. 3, a plurality of the beam shaping devices 24 may be arranged symmetrically about a common reference axis 50. In one embodiment of the invention, the beam shaping devices 24 may be arranged such that the common reference axis 50 coincides with the axis of revolution 30. In addition or alternatively, the beam shaping devices 24 may be arranged such that the focal points 18 of the beam shaping devices 24 generally coincide. As seen in FIG. 3, in such an embodiment, the energy waves would be concentrated at a common focus 18 on axis 50 (which may coincide with axis 30).

Figure 4:
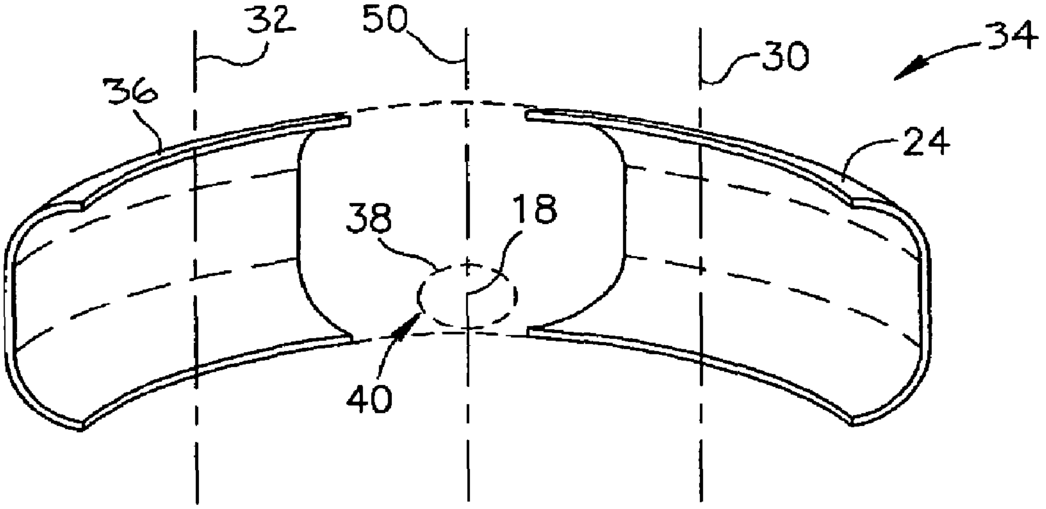
FIG. 4 is a simplified illustration of a wave generating device of FIG. 3 constructed and operative in accordance with another embodiment of the invention, comprising beam shaping devices (e.g., reflector segments) with different focal points.

Reference is now made to FIG. 4, which illustrates a wave generating device 34, which is a variant of the wave generating device 24 of FIG. 3, in accordance with another embodiment of the invention. (In FIG. 4, the wave transducer is omitted for the sake of clarity.) Wave generating device 34 may comprise beam shaping devices (e.g., reflector segments) that have different focal points or which are revolved about differently distanced axes of revolution. For example, a beam shaping device 36 may be formed by revolution about an axis of revolution 32, which is distanced differently from wave transducer 11 than axis of revolution 30. Additionally or alternatively, beam shaping device 36 may have a different focusing power or properties than beam shaping device 24.

One result of this construction may be that focal points 18 and 38 of beam shaping devices 24 and 36, respectively, do not coincide. Accordingly, as seen in FIG. 4, a locus 40 of the focal points of the beam shaping devices 24 and 36 (and others which may form a wave delivery system) generally lies in a single plane, and may form a torus or other shape.

Figure 5:
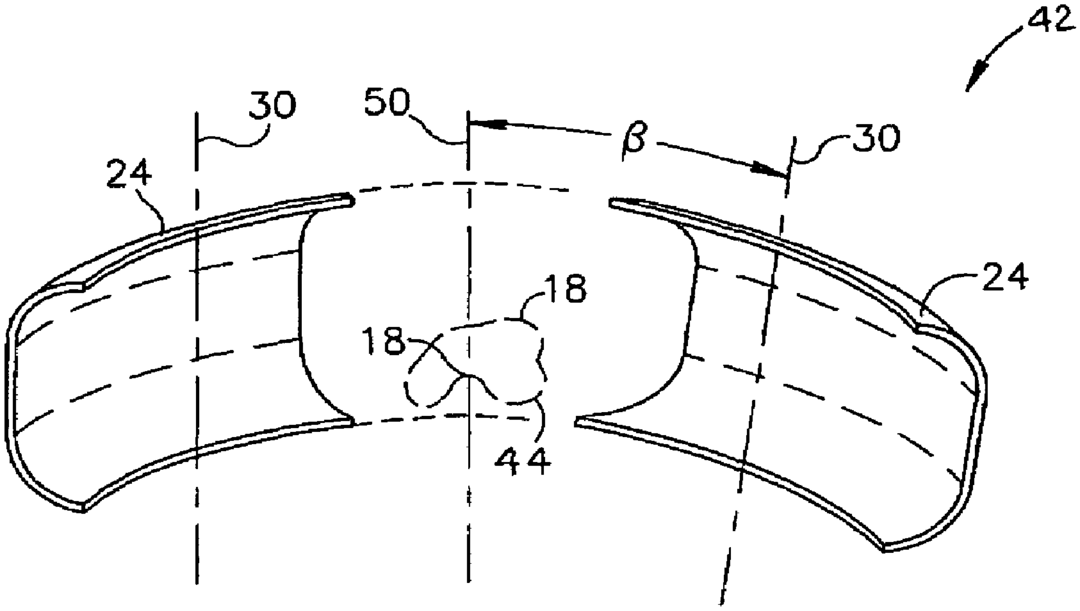
FIG. 5 is a simplified illustration of a wave generating device of FIG. 3 constructed and operative in accordance with yet another embodiment of the invention, comprising beam shaping devices (e.g., reflector segments) aimed at different points.

Reference is now made to FIG. 5, which illustrates a wave generating device 42, which is yet another variant of the wave generating device 24 of FIG. 3, in accordance with another embodiment of the invention. (In FIG. 5, the wave transducer is omitted for the sake of clarity.) In this embodiment, wave generating device 42 may comprise beam shaping devices 24 aimed at different points. This may be accomplished by mounting the beam shaping devices 24 such that they are movable independently of one another. A controller and actuator apparatus (not shown) may be coupled to the beam shaping devices 24 for independently controlled motion of the devices 24.

For example, in the illustrated embodiment, one of the beam shaping devices 24 is tilted at an angle $\beta$ with respect to axis 50, whereas another beam shaping device 24 is not tilted with respect to axis 50. It is seen that in such an embodiment, a locus 44 of the focal points 18 of the beam shaping devices 24 does not lie in a single plane.

Figure 6:
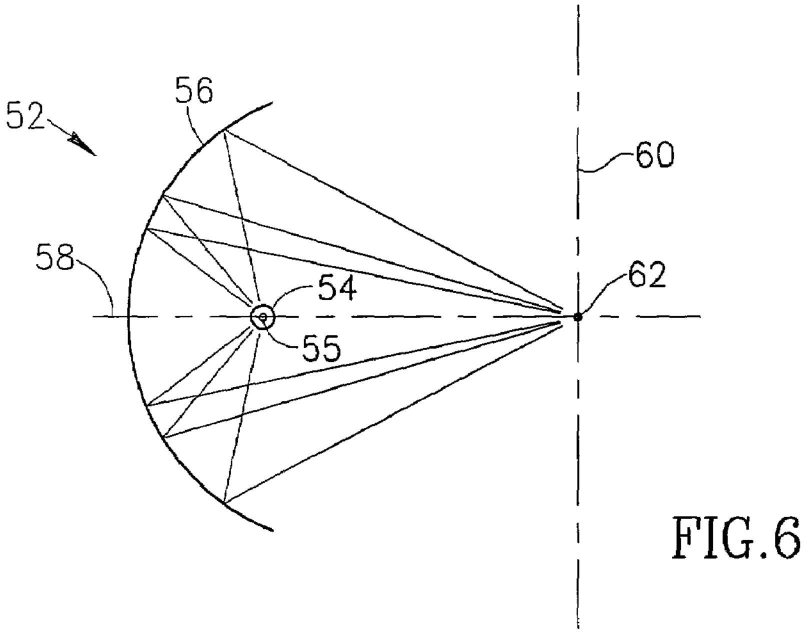
FIG. 6 is a simplified cross-sectional illustration of a wave generating device, comprising a point source wave transducer (or circular source wave transducer whose center is at the first focus of an ellipse) and an ellipsoidal reflector having an axis of symmetry.

Reference is now made to FIG. 6, which illustrates a wave generating device 52, comprising a wave transducer 54 and an ellipsoidal reflector 56 having an axis of symmetry 58. The wave transducer 54 may comprise a point source wave transducer or a circular source wave transducer whose center is at a first focus 55 of the ellipse that defines ellipsoidal reflector 56. The wave transducer 54 may discharge energy at the first focus 55, and the waves may be focused by reflector 56 onto a second focus 62.

Figure 7:
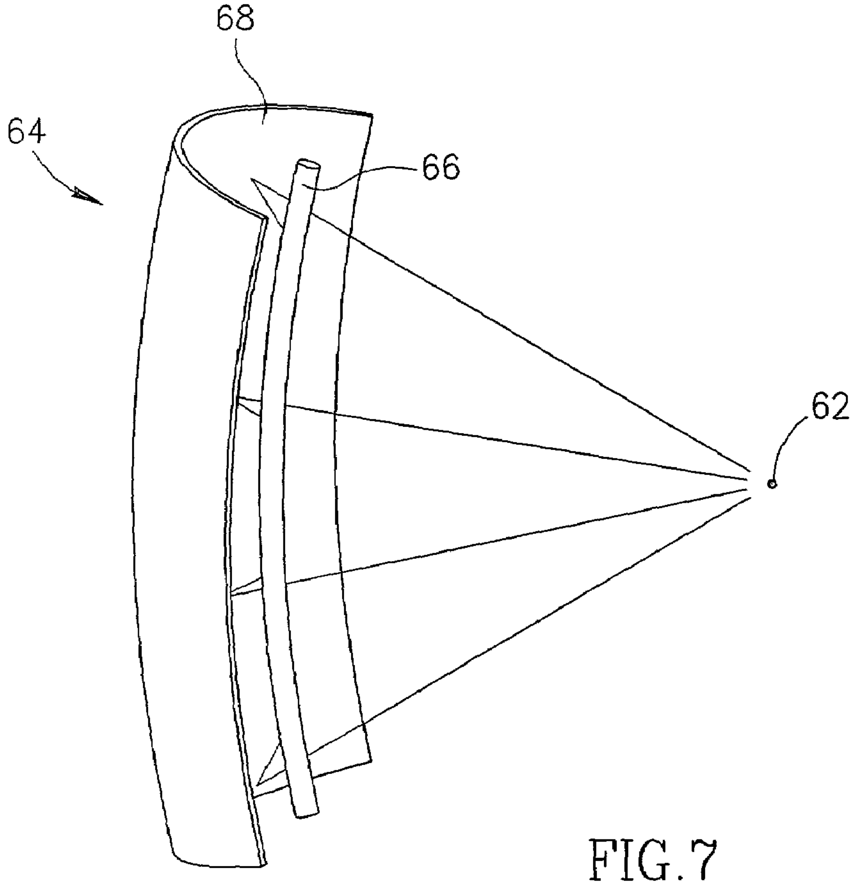
FIG. 7 is a simplified illustration of a wave generating device constructed and operative in accordance with another embodiment of the invention, wherein the wave transducer and the ellipsoidal reflector of FIG. 6 are revolved about an axis of revolution different from their axis of symmetry.

Reference is now made to FIG. 7, which illustrates a wave generating device 64, constructed and operative in accordance with another embodiment of the invention. Wave generating device 64 may comprise a wave transducer 66 and a reflector 68 respectively formed by revolving the wave transducer 54 and the ellipsoidal reflector 56 of FIG. 6 about an axis of revolution 60 (FIG. 6) different from (not collinear with) their axis of symmetry 58.

Figure 8:
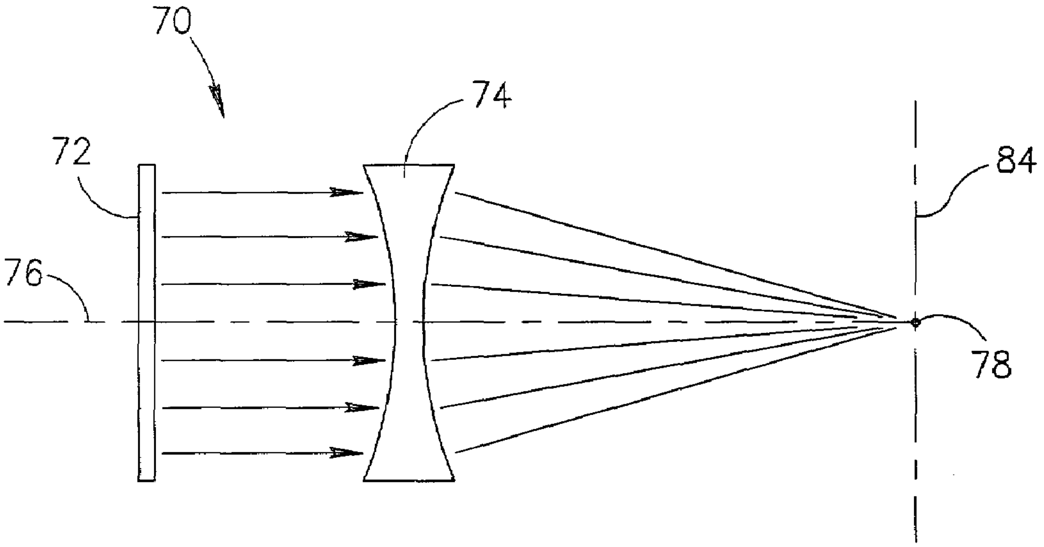
FIG. 8 is a simplified cross-sectional illustration of a wave generating device, comprising a planar source wave transducer and a concave focusing lens having an axis of symmetry.

The previously described embodiments of the present invention may comprise reflectors as the beam shaping device. Reference is now made to FIG. 8, which illustrates a cross-section of a wave generating device 70, which may comprise a different kind of beam shaping device. Wave generating device 70 may comprise a planar source wave transducer 72, such as but not limited to, electromagnetic apparatus (e.g., a repulsive membrane). Wave generating device 70 may comprise a beam shaping device in the form of a concave focusing lens 74 having an axis of symmetry 76. Lens 74 may focus waves emanating from wave transducer 72 to a focal point 78.

Figure 9:
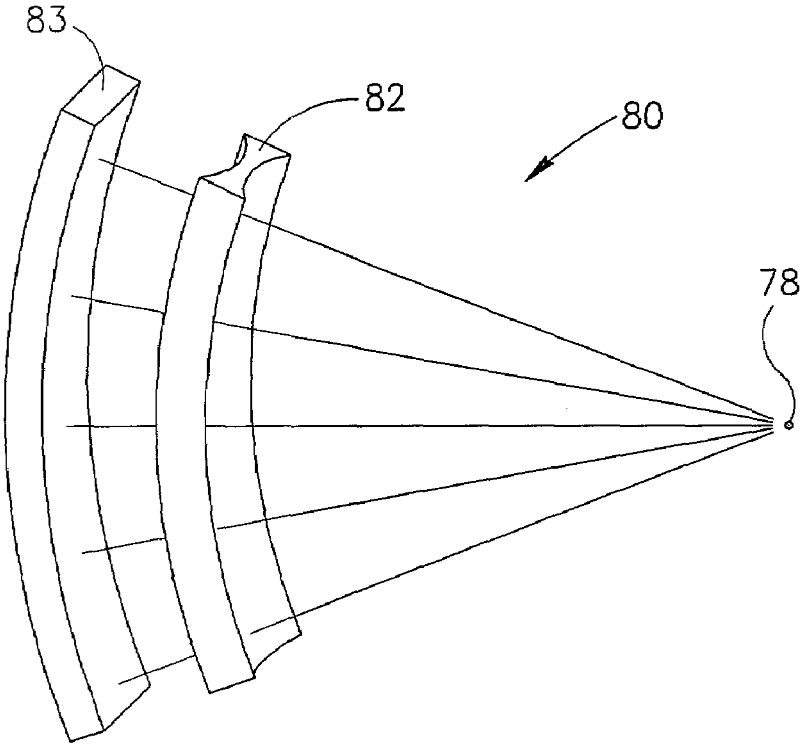
FIG. 9 is a simplified illustration of a wave generating device constructed and operative in accordance with still another embodiment of the invention, wherein the planar source wave transducer and the focusing lens of FIG. 8 are revolved about an axis of revolution different from their axis of symmetry.

Reference is now made to FIG. 9, which illustrates a wave generating device 80, constructed and operative in accordance with still another embodiment of the invention. Wave generating device 80 may comprise a beam shaping device 82 and a wave transducer 83 defined by revolution of lens 74 and wave transducer 72, respectively, about an axis of revolution 84 (FIG. 8) different from (not collinear with) their axis of symmetry 76.

It will be appreciated by person skilled in the art, that the present invention is not limited by what has been particularly shown and described herein above. Rather the scope of the present invention is defined only by the claims that follow:

What is claimed is:

1. A wave generating device comprising:

a wave transducer adapted to generate an energy wave; and a beam shaping device comprising a lens defined by revolution of a curve about an axis of revolution, said curve being arranged with respect to said transducer in a plane of said curve so as to focus a wave emanating from said transducer towards said beam shaping device to a focal point lying in said plane, said curve having an axis of symmetry in said plane, wherein said axis of revolution is generally not collinear with said axis of symmetry, and wherein said wave transducer is formed by a shape revolved about said same axis of revolution.

2. The wave generating device according to claim 1 wherein said curve comprises a portion of a conic section.

3. The wave generating device according to claim 2 wherein said portion of a conic section comprises at least a portion of at least one of a parabola, an ellipse, a circle and a hyperbola.

4. The wave generating device according to claim 1 and further comprising a plurality of said beam shaping devices.

5. The wave generating device according to claim 4 wherein said beam shaping devices are arranged symmetrically about a common reference axis.

6. The wave generating device according to claim 5 wherein said common reference axis comprises said axis of revolution.

7. The wave generating device according to claim 4 wherein said focal points of said beam shaping devices generally coincide.

8. The wave generating device according to claim 4 wherein said focal points of said beam shaping devices do not coincide.

9. The wave generating device according to claim 4 wherein a locus of said focal points of said beam shaping devices generally lies in a single plane.

10. The wave generating device according to claim 4 wherein a locus of said focal points of said beam shaping devices does not lie in a single plane.

11. The wave generating device according to claim 4 wherein one of said beam shaping devices is movable independently of another of said beam shaping devices.

12. The wave generating device according to claim 4 wherein one of said beam shaping devices is formed by revolution about an axis of revolution which is distanced differently from its wave transducer than the distance from the axis of revolution to the wave transducer of another of said beam shaping devices.

13. The wave generating device according to claim 4 wherein the locus of said focal points of said beam shaping devices form a torus.

14. The wave generating device according to claim 1 wherein a cross-section of said wave transducer in said plane comprises a straight edge.

15. The wave generating device according to claim 1 wherein a cross-section of said wave transducer in said plane comprises a curved edge.

16. The wave generating device according to claim 1 wherein a cross-section of said wave transducer in said plane comprises two portions distanced from each other and symmetrical about said axis of symmetry.

17. A system comprising:

a wave transducer adapted to generate an energy wave;

a beam shaping device comprising a lens defined by revolution of a curve about an axis of revolution, said curve being arranged with respect to said transducer in a plane of said curve so as to focus a wave emanating from said transducer towards said beam shaping device to a focal point lying in said plane, said curve having an axis of symmetry in said plane, wherein said axis of revolution is generally not collinear with said axis of symmetry, and wherein said wave transducer is formed by a shape revolved about said same axis of revolution; and an imaging probe adapted to provide images at least in a vicinity of said focal point.

18. The system according to claim 17 wherein said imaging probe is formed by a shape revolved about said same axis of revolution.

* * * * *